United States Patent [19]

Yang

[11] Patent Number: 5,612,621
[45] Date of Patent: Mar. 18, 1997

[54] METHOD FOR MONITORING CRACKS AND CRITICAL CONCENTRATION BY USING PHASE ANGLE

[75] Inventor: Iuan-Jou Yang, Hsinchu, Taiwan

[73] Assignee: Industrial Technology Research Institute, Taiwan

[21] Appl. No.: 967,209

[22] Filed: Oct. 27, 1992

[51] Int. Cl.⁶ .................................................. G01N 27/20
[52] U.S. Cl. .................. 324/439; 324/700; 324/709; 324/718; 204/404; 205/775.5; 205/777; 205/791.5
[58] Field of Search .............................. 204/129.2, 129.4, 204/129.43, 401, 404; 324/221, 233, 439, 442, 444, 700, 709

[56] References Cited

U.S. PATENT DOCUMENTS

| | | | |
|---|---|---|---|
| 3,661,748 | 5/1972 | Blackmer | 324/425 |
| 4,266,185 | 5/1981 | Charlesworth | 324/716 |
| 4,683,419 | 7/1987 | Neuelmann | 324/718 |
| 4,777,444 | 10/1988 | Beijk | 324/439 |
| 4,881,031 | 11/1989 | Pfisterer | 324/233 |
| 5,059,905 | 10/1991 | Drits | 324/233 |
| 5,184,071 | 2/1993 | Tasca | 324/233 |

FOREIGN PATENT DOCUMENTS 0126147   5/1990   Japan ...................... 324/718

*Primary Examiner*—Kenneth A. Wieder
*Assistant Examiner*—Jose M. Solis
*Attorney, Agent, or Firm*—Marshall & Melhorn

[57] ABSTRACT

A method for monitoring cracks in a sample of materials by applying the theory that the phase angle increases in the sample of materials being tested where cracks have formed. The method is performed by preparing a solution capable of forming cracks in the sample, preparing an auxiliary electrode, then making the sample and the auxiliary electrode contact with the solution, preparing a frequency generator connecting the sample and the auxiliary electrode respectively, choosing a frequency, and turning on the frequency generator with an alternating current of the frequency, monitoring the phase angle measured in the sample, and determining the formation of cracks in the sample by checking whether the phase angle measured in the sample increases with time. Similarly, a method for monitoring the critical concentration of a solution can be obtained by gradually increasing the concentration of the solution and repeating the above mentioned steps, until an increase in the phase angle measured in the sample is found.

14 Claims, 15 Drawing Sheets

METHOD FOR MONITORING CRACKS AND CRITICAL CONCENTRATION BY USING PHASE ANGLE

BACKGROUND OF THE INVENTION

The present invention relates to a method for monitoring cracks in a sample of materials by using phase angle, and the method for monitoring cracks by using phase angle can be used to determine the critical concentration of a solution, the concentration being capable of forming cracks in a sample of materials.

Materials always have the possibility of forming cracks, for example, some materials may demonstrate sensitization in the welding process. If a corrosive ion such as chloride ion solution is added at this time, the materials will be corroded and form cracks.

An European Patent No. 70124 describes a method of detecting and quantifying damage in metal structures by using the strain electrometric technique to measure the local surface potential of a specimen. However, this method must require an electrolytic cell wherein, as one electrode, the metal structure to be monitored and at least one reference electrode are at least partially immersed in an electrode having properties which cause passivation of the immersed surface of the metal structure and at least partial de-passivated thereof when a flow of current to the passivated surface is established, and once the surface has become initially passivated, detecting any change in the electrochemical potential of the immersed metal structure. The passivation characteristics of the monitored metal must be known before applying this method, thus this causes some inconveniences in application.

A U.S. Pat. No. 4,048,558 describes a method and apparatus for detecting metal failures in situ. The method comprises making measurements of an electrical characteristics of a circuit including a section of the metal structure at different applied frequencies. Through such measurement, it is possible to detect cracks and follow their progress as they deepen. Because of skin effect, the impedance change resulting from cracks in the surface of the metal will be detected, and by monitoring the impedance at each of these frequencies the depth of a crack can be determined as long as it has a transverse component. However, in order to measure the impedance change, the metal to be tested must be welding a signal receiving point. In addition, the environment of the metal to be tested, for example, temperature and the flow speed of the liquid can affect the response of the signals.

A French Patent No. 2,274,042 describes a method for monitoring the defective metal. This method uses a probe with two impedance settings connected on an AC impedance bridge, and the impedance is changed to generate an output potential change, so as to monitor the defective metal. However, the probe must be applied to the method, the probe may be corroded by the testing metal having corrosive properties and affect the accuracy of the output potential.

A U.S. Pat. No. 4,307,610 describes a method for measuring crack propagation in samples with a high frequency pulsator, but this method uses only in load cycle cases.

SUMMARY OF THE INVENTION

It is an object of the present invention to provide a method for monitoring cracks in a sample of materials by using phase angle.

It is another object of the present invention to provide a method for monitoring the critical concentration of a solution, the concentration being capable of forming cracks in a sample of materials.

In accordance with the present invention, an alternating impedance theory is applied. Suppose that a sample surface to be tested is a resistor, R and a capacitor, C, connected in series or in parallel, and the phase angle measured in the sample changes with different frequencies. Similarly, the phase angle measured in the sample also changes with a constant frequency but different values of the supposed resistor, R, or capacitor, C, of the sample surface to be tested. FIG. 1A is a schematic circuit diagram for the present invention to apply the theory, wherein $R\Omega$ indicates the resistance of the solution, R indicates the resistance of the sample surface to be tested, C indicates the capacitor. The electrical circuit of FIG. 1A can be expressed as follows:

$$Z=Z'+j\cdot Z''=R\Omega+R/(1+j\cdot w\cdot R\cdot C) \qquad (1)$$

$w=2\cdot\pi\cdot f$, f indicates the frequency, $\Theta$ indicates the phase angle, and $$\tan\Theta=1/(w\cdot R\cdot C) \qquad (2)$$

The influence intensity of the change of R or C relatives to the phase angle can be calculated from equation (2).

When R is a variable, the phase angle does not increase with time, as shown in FIG. 1B. When C is a variable, the phase angle increases with certain frequencies, as shown in FIG. 1C. In other words, the value of the capacitor, C, changes when a crack forms in the sample to be tested, and the capacitor value increases as the crack propagates, the phase angle with constant frequency measurement also be changed.

Basing on the principle, the present invention provides a method for monitoring cracks in a sample of materials and a method for monitoring the critical concentration of a solution, the concentration being capable of forming cracks in a sample of materials.

The method for monitoring cracks comprises an auxiliary electrode in a suitable solution that can form cracks in the sample (examples of the suitable solution are a solution containing chlorine ion, a solution containing sulfur environment, etc.). The sample contacts with the solution and a frequency is chosen from a frequency generator which connects the sample and the auxiliary electrode. Then turn on the frequency generator with an alternating current of the frequency and monitor the phase angle measured in the sample. If the phase angle measured in the sample increases with time, we will know that the crack forms in the sample.

And the method for monitoring critical concentration comprises a sample and an auxiliary electrode that contact with a solution, where the concentration is capable of forming cracks in the sample (examples of the solution are a solution containing chlorine ion, a solution containing sulfur environment, etc.). A frequency is chosen from a frequency generator which connects the sample and the auxiliary electrode. Turn on the frequency generator with an alternating current of the frequency and monitor the phase angle measured in the sample. Increase the concentration of the solution if the phase angle measured in the sample doesn't increases with time. And repeat the above steps till that the phase angle measured in the sample increases. So the stated objects are achieved.

FIG. 2 is a testing system diagram of a preferred embodiment in the present invention, wherein 10 indicates the sample to be tested, 20 indicates the solution, 30 indicates the auxiliary electrode. FIG. 3 shows a procedure diagram of the method for monitoring cracks of the preferred embodiment in the present invention in FIG. 2.

BRIEF DESCRIPTION OF THE DRAWINGS

The present invention can be more fully understood by reference to the following description and accompanying drawings, wherein.

DETAILED DESCRIPTION OF THE PREFERRED EMBODIMENTS

Experiment 1

Figure 1A:
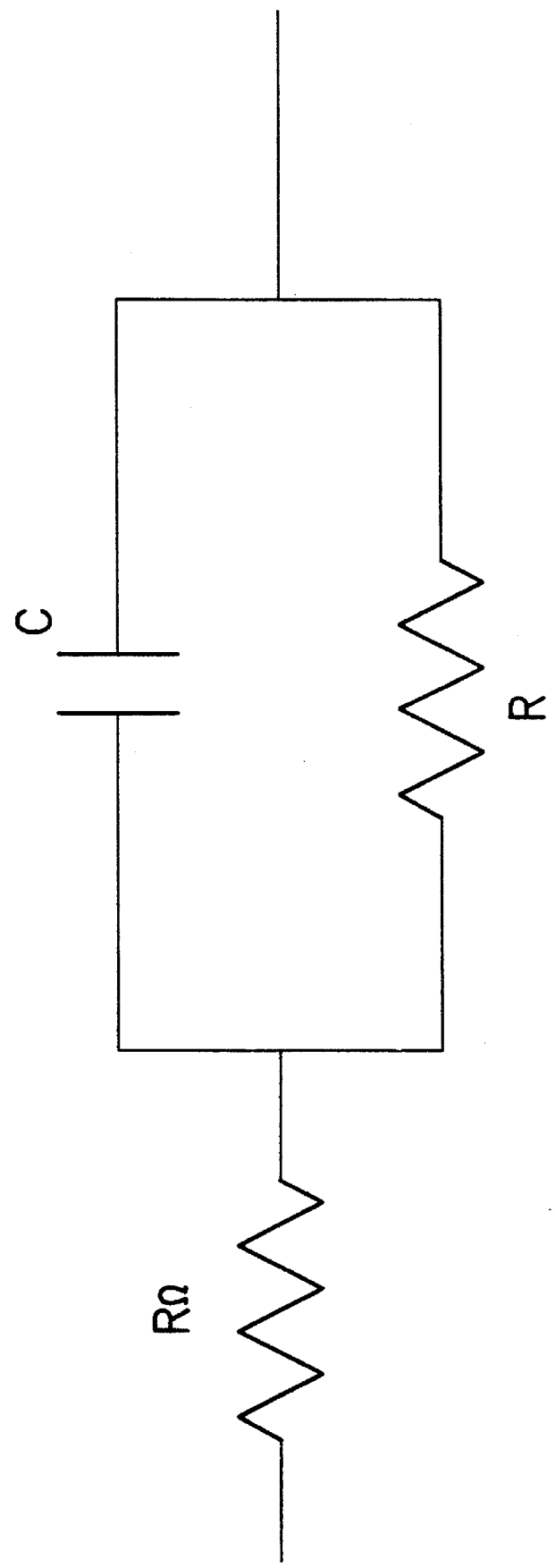
FIG. 1A is a schematic circuit diagram for the present invention to apply the theory.
Figure 1B:
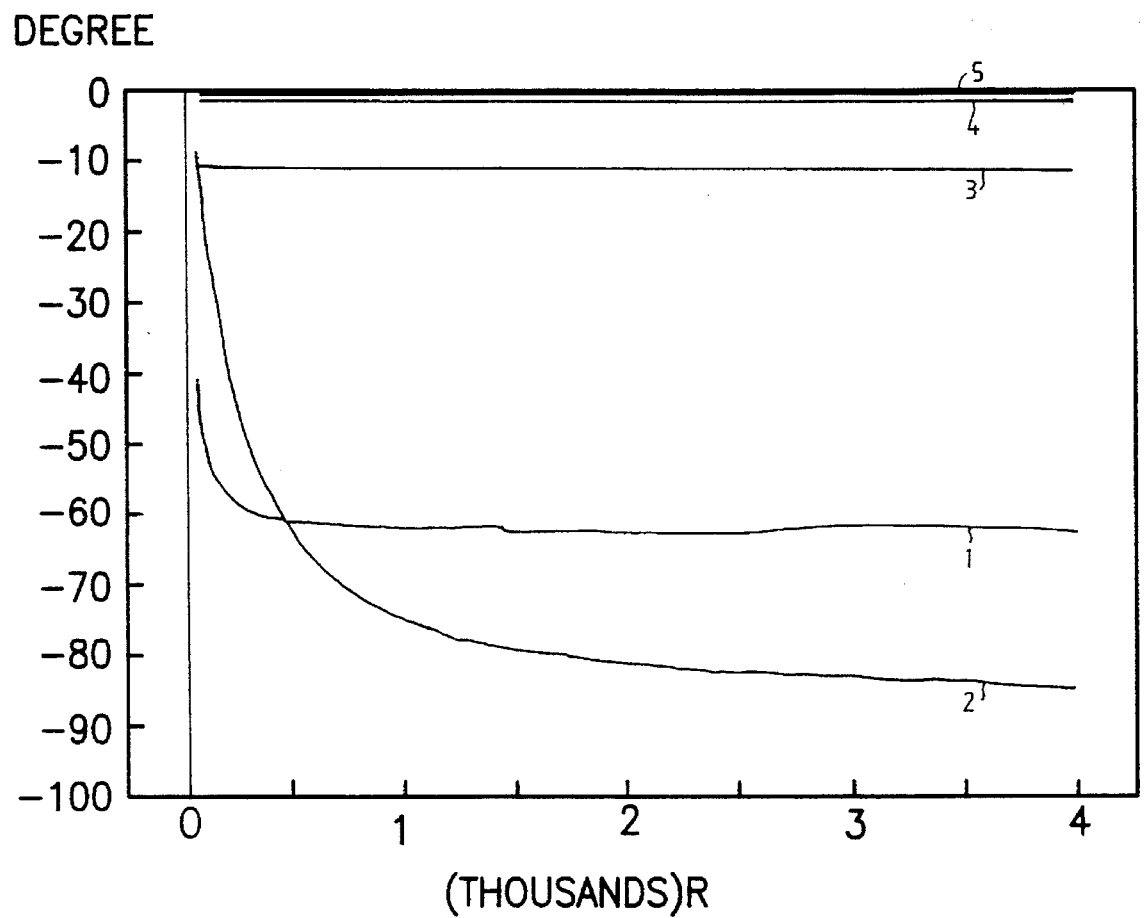
FIG. 1B is a relation diagram between phase angle and R when a sample shown in FIG. 1A has no crack.
Figure 1C:
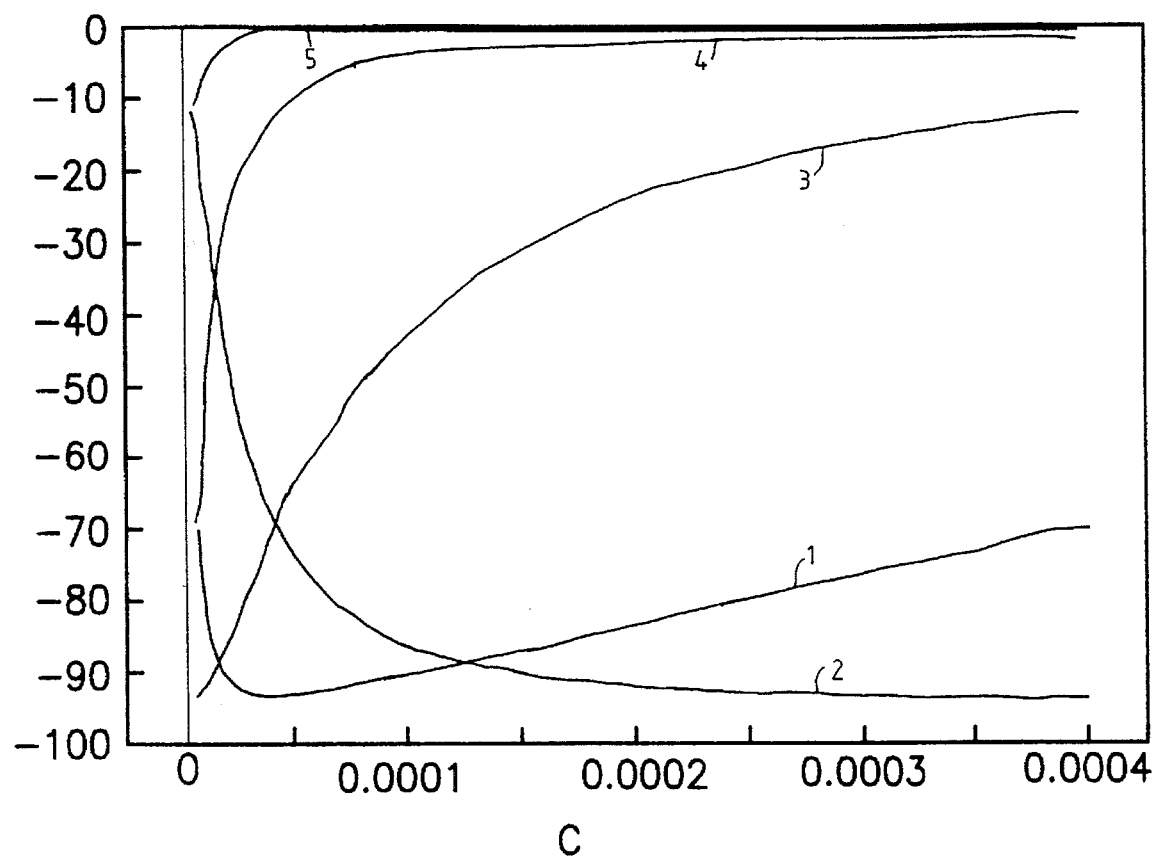
FIG. 1C is a relation diagram between phase angle and C when the sample shown in FIG. 1A has a crack.
Figure 2:
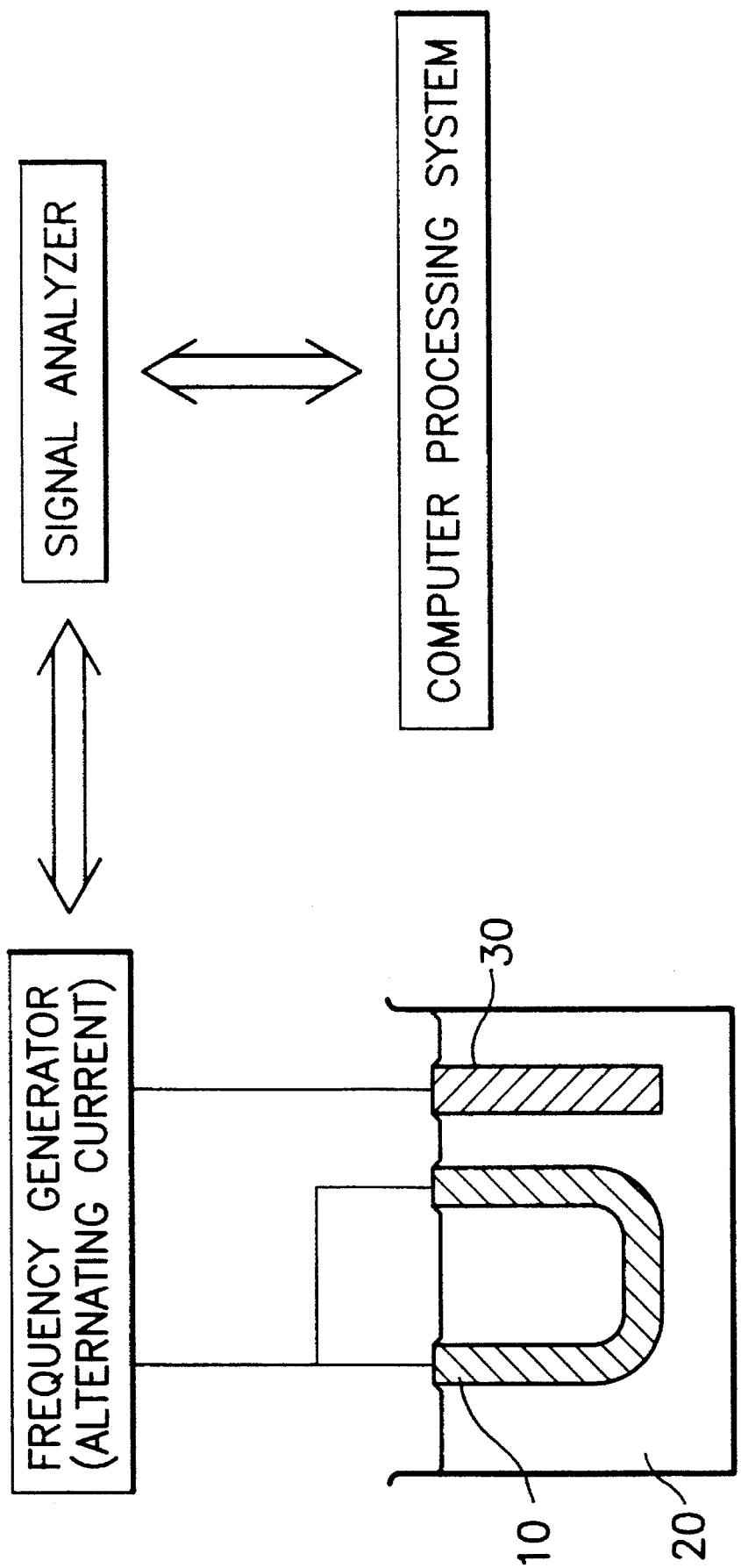
FIG. 2 is a testing system diagram of a preferred embodiment in the present invention.
Figure 3:
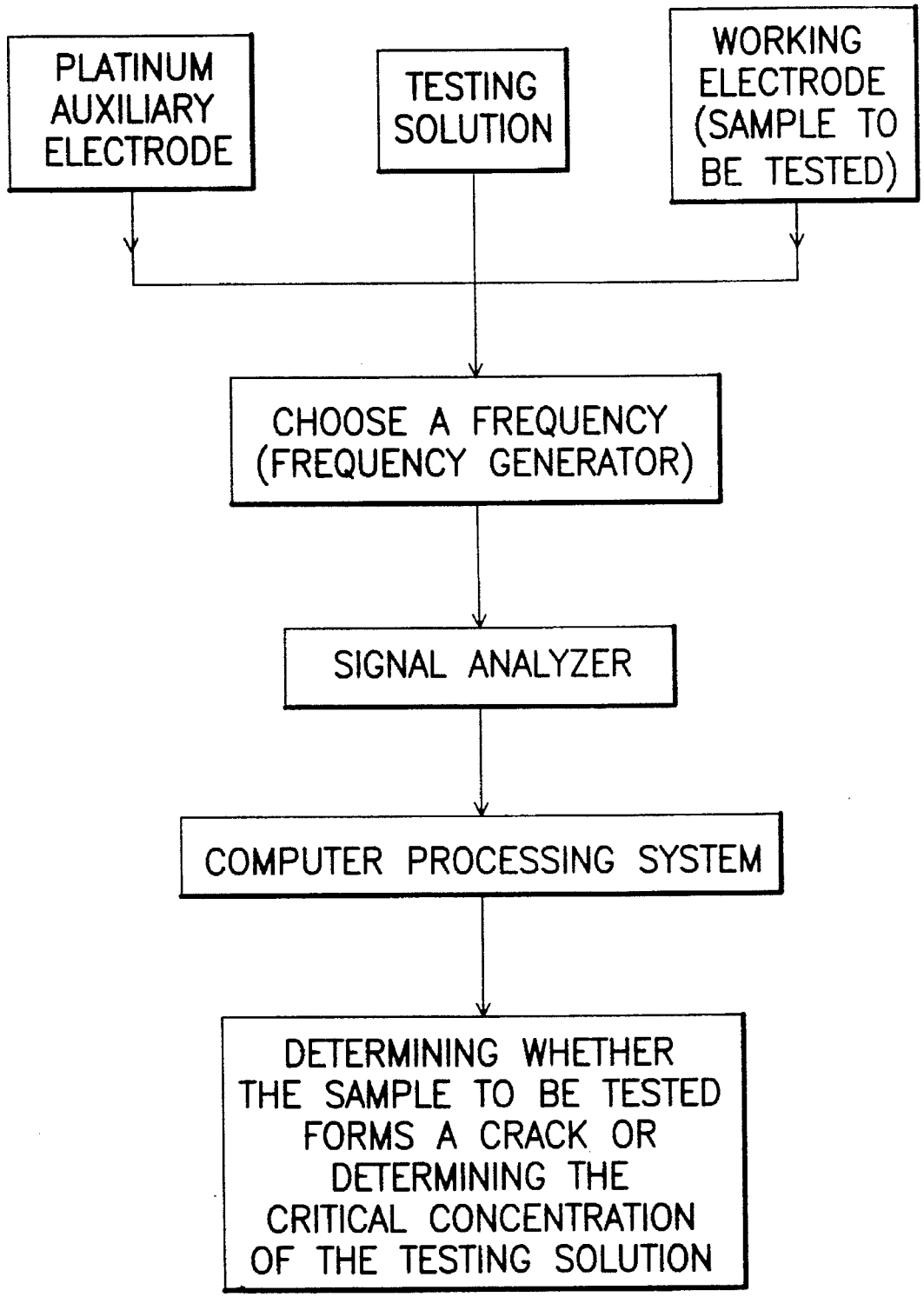
FIG. 3 shows a procedure diagram of the method for monitoring cracks of the preferred embodiment in the present invention in FIG. 2.
Figure 4:
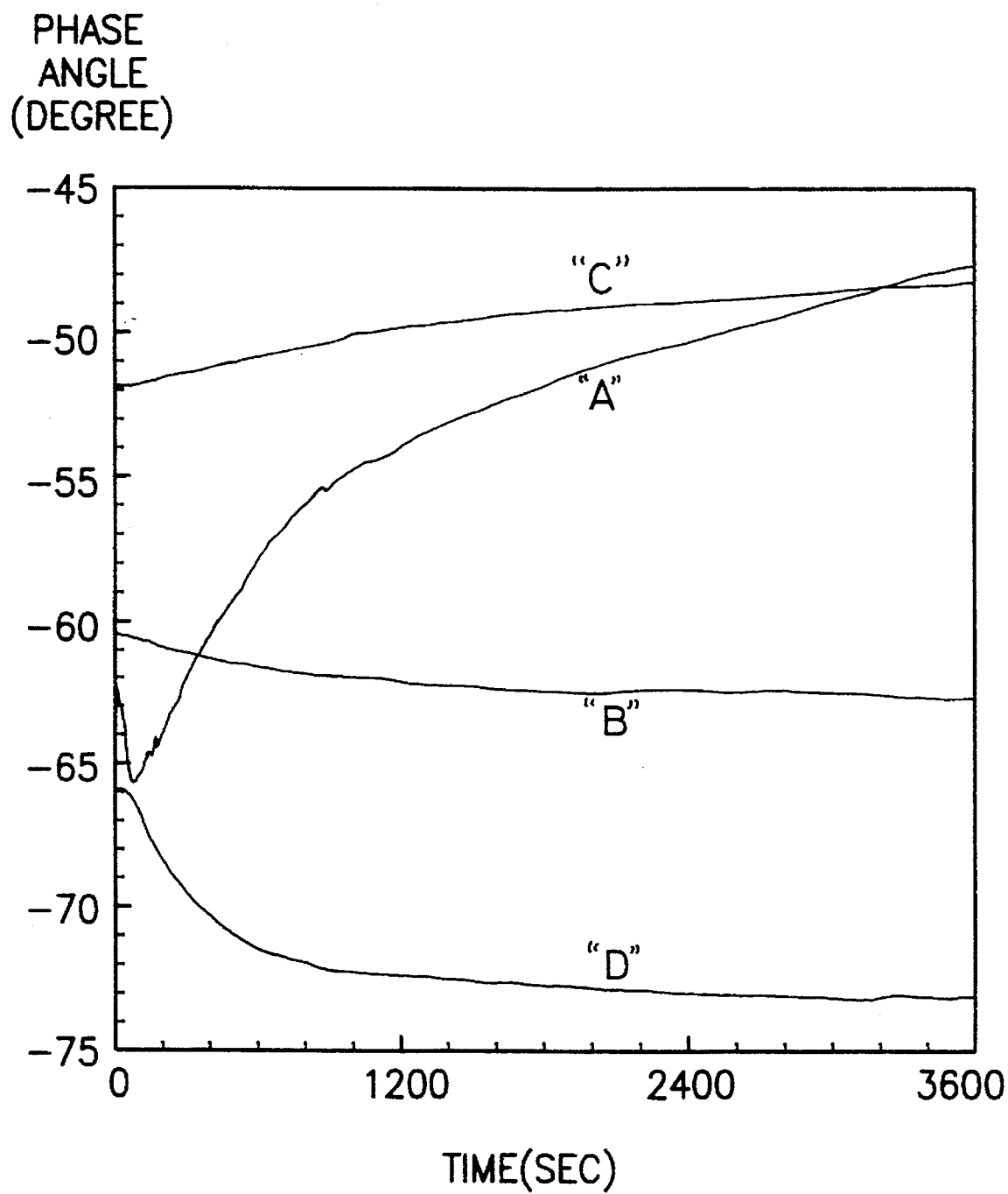
FIG. 4 is a relation diagram between phase angle and time for different states of stainless steels immersed into $Na_2S_2O_3$ solution when the frequency is 20 Hz.
Figure 5A:
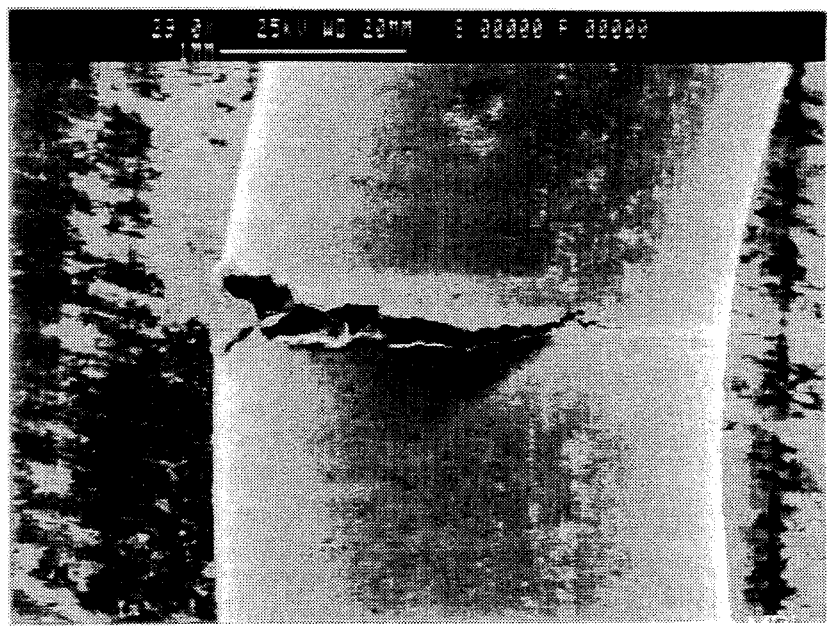
FIG. 5A is a magnified diagram of a crack formed on the outline of the sensitized 304 stainless steel.
Figure 5B:
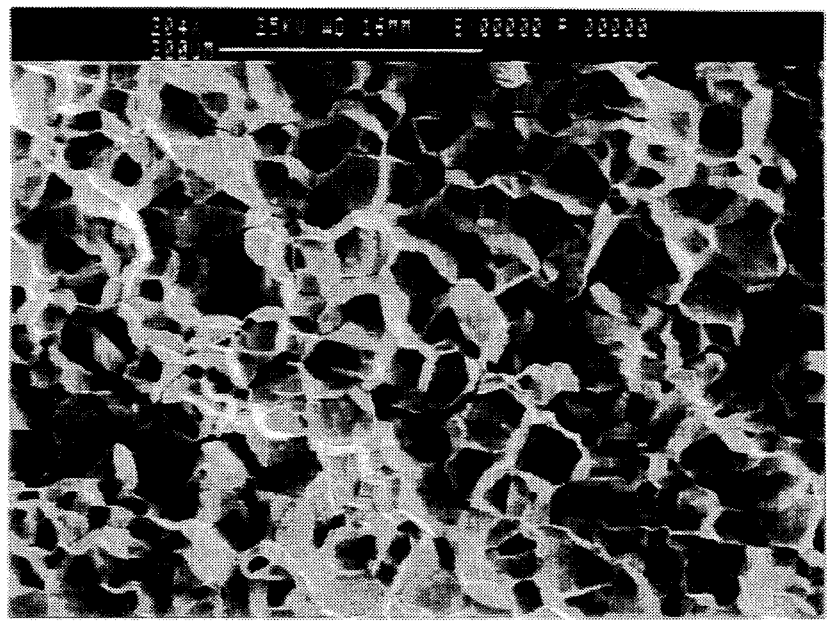
FIG. 5B shows a typical crack cross section IGSCC (Intergranular stress Corrosion Cracking) type of the U-type sensitized 304 stainless steel.
Figure 6:
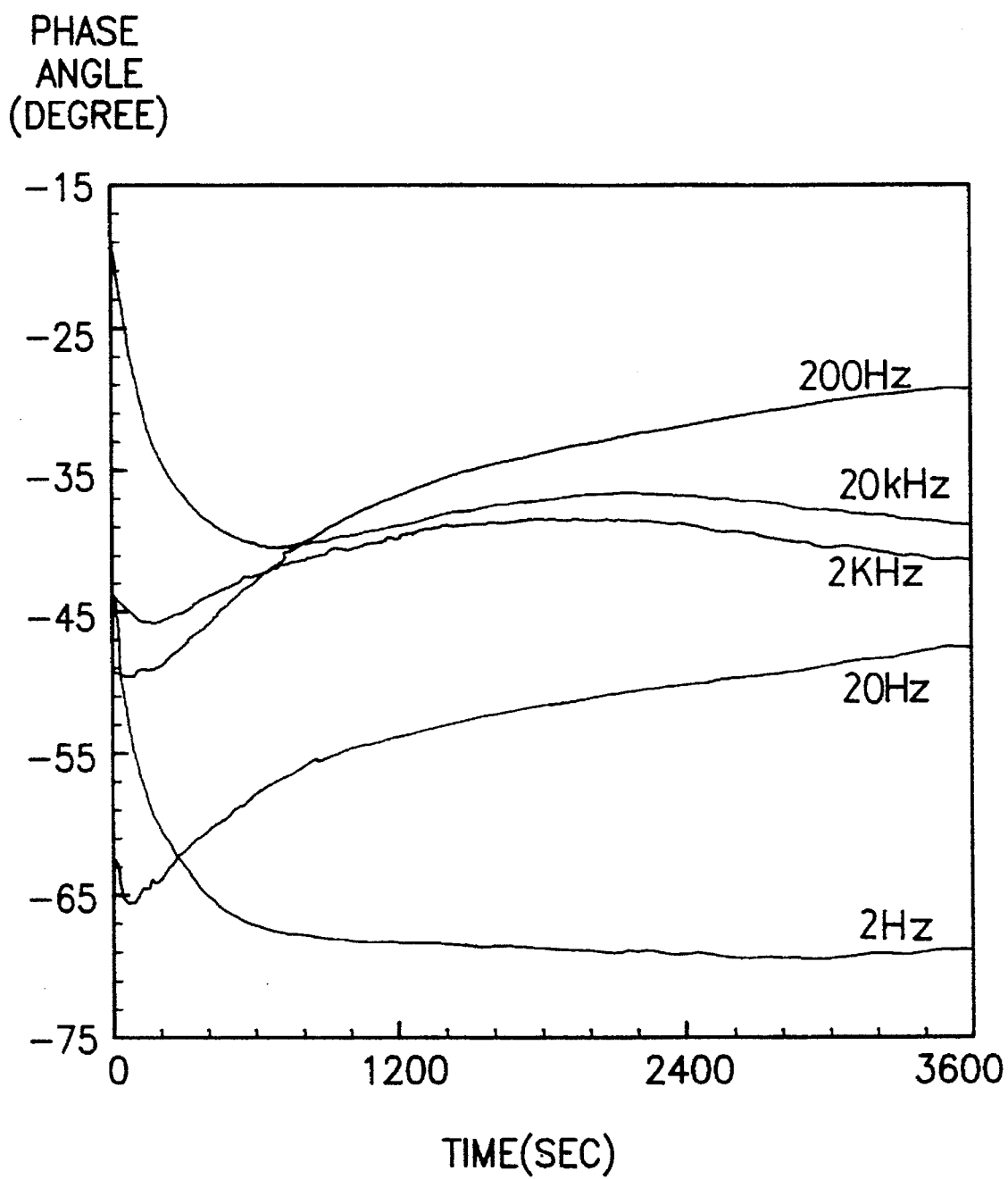
FIG. 6 is a relation diagram between phase angle and time for immersing the U-type sensitized 304 stainless steel into $Na_2S_2O_3$ solution when the frequency is between 20 KHz and 2 Hz.
Figure 7:
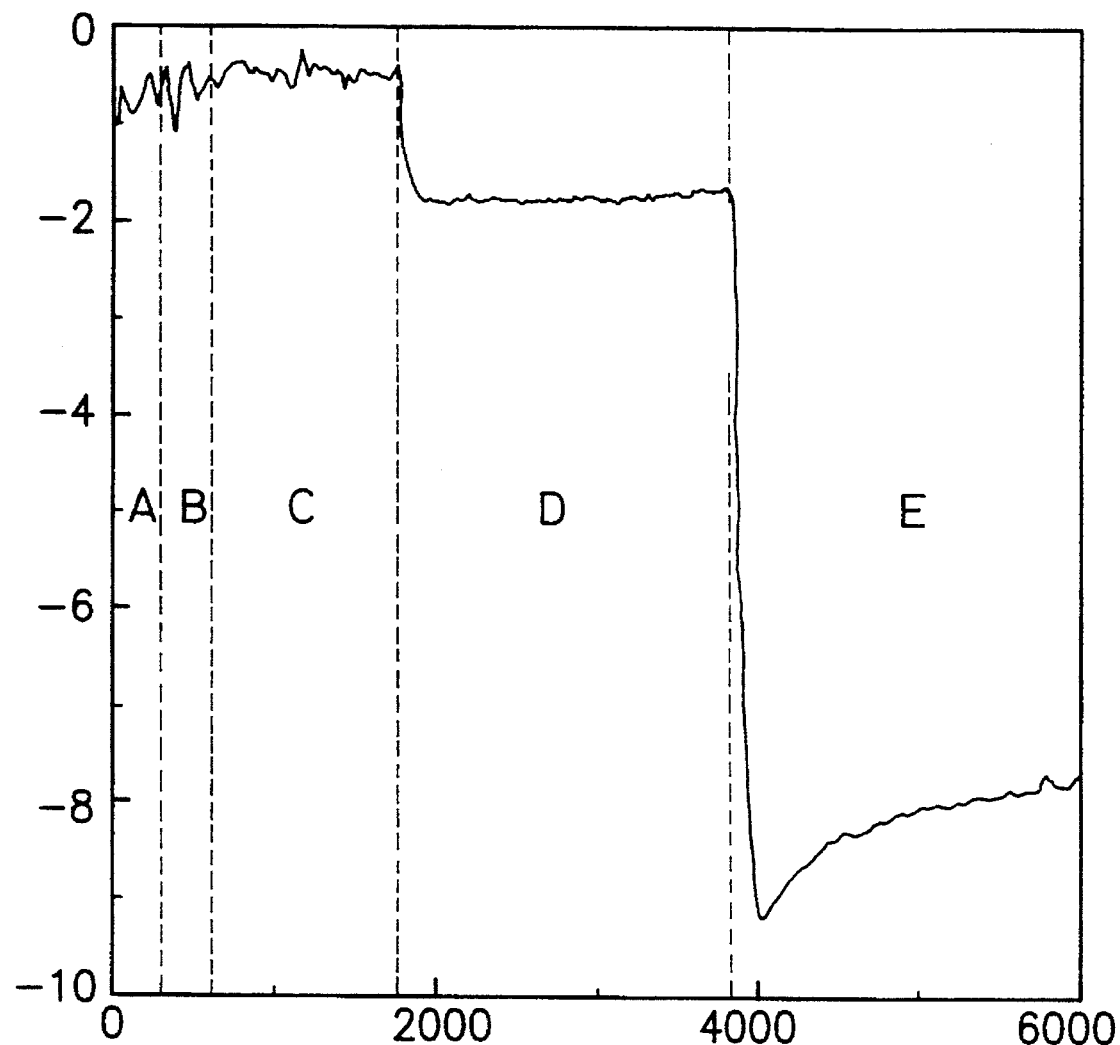
FIG. 7 is a relation diagram between phase angle and time for the U-type sensitized 304 stainless steel corresponding to the different concentration of $Na_2S_2O_3$ solution.

(1) Testing conditions
  Sample: sensitized 304 stainless steel and unsensitized 304 stainless steel
  Testing solution: 0.5M $Na_2S_2O_3$
  Temperature: 50° C.
  Frequency: 20 Hz
(2) Crack monitoring
  When the immerse time beyond 60 seconds, the phase angle of the U-type sensitized 304 stainless steel sample begins to climb, and the phase angle increases as the crack propagates, this is shown in line "A" of FIG. 4. As the immersion time increases, the phase angle of the unsensitized 304 stainless steel declines and tends to level off, as shown in line "B" of FIG. 4. After testing, the outline of the unsensitized 304 stainless steel sample is still the same, but the outline of the sensitized 304 stainless steel forms a crack as shown in FIG. 5A. The crack cross section is a typical of IGSCC (Intergranular stress Corrosion Cracking) type as shown in FIG. 5B.
(3) The influence of corrosive process
  Following the test in line "A", the U-type sample is divided into two halves, and one of them is immersed into the testing solution to study the effect of corrosion on phase angle. Measure the phase angle change of the sample while the frequency is set at 20 Hz, the results indicate there is no obvious change in the phase angle as shown in line "C" of FIG. 4. It is clear that an increase in the phase angle is mainly caused by the crack propagation, not the corrosive process.
  The sensitized 304 stainless steel sample, not subjected to force, i.e. not bent, is immersed into the testing solution. The phase angle change of the sample is measured while the frequency is 20 Hz, and the results indicate the phase angle declines initially but lastly tends to level off as shown in line "D" of FIG. 4. Thus, this is another proof that an increase in the phase angle is mainly caused by the crack propagation but not the corrosive process.
(4) Appropriate frequency
  Immerse the U-type sensitized 304 stainless steel sample in the testing solution, and observe the phase angle change with different frequencies, i.e. 20 KHz to 2 Hz. In general, all the U-type samples showed IGSCC (Intergranular stress Corrosion Cracking) crack after immersion for 3600 seconds, but there are obvious changes in the phase angle. As shown in FIG. 6, when the frequency $\geq 2$ KHz, the phase angle increases initially but ultimately declines, and when the frequency $\leq 2$ Hz, the phase angle declines initially but then tends to level off. This phenomenon is due to the characteristics of the AC Impedance: The aim of the high frequency is to study the solubility of the testing solution, the characteristics of the testing matter surface cannot be shown if the frequency is too low, the crack of the matter surface and the characteristics of its propagation can be shown only under an appropriate range of frequencies.
(5) The decision of a critical concentration
  Besides monitoring the crack and its propagation, the present invention can be used to decide the critical anion concentration of forming the crack. Immerse the U-type sensitized 304 stainless steel sample into $Na_2S_2O_3$ at 50° C., and an alternating current with frequency of 200 Hz is applied to it. The phase angle change as shown in FIG. 7, wherein the concentration of $Na_2S_2O_3$ in: A is 0 ppm, B is 100 ppb, C is 1 ppm, D is 10 ppm, E is 100 ppm. When the concentration of $Na_2S_2O_3 \leq 10$ ppm, the phase angle remains a stable value. When the concentration of $Na_2S_2O_3 \geq 100$ ppm, the phase angle declines initially due to the conductivity change of the testing solution, but after a period of time, the phase angle begins to climb, indicating the U-type sensitized 304 stainless steel has formed a crack in 100 ppm $Na_2S_2O_3$ concentration.

Experiment 2

(1) Testing conditions

Sample: copper-zinc alloy (70/30 Brass)

Testing solution: $NH_4OH$

Temperature: room temperature (2) Crack monitoring

Figure 8:
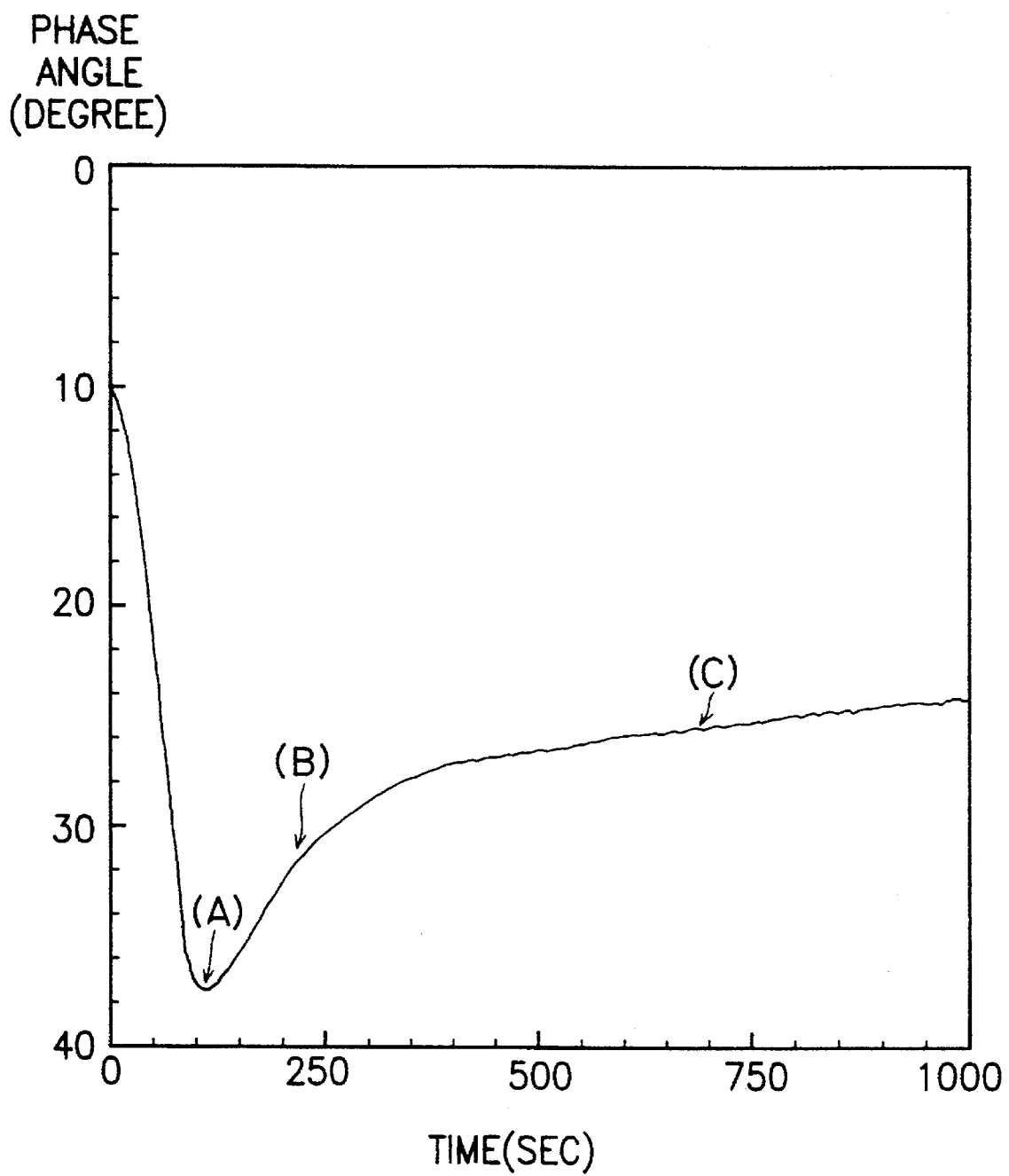
FIG. 8 is a relation diagram between phase angle and time for the copper-zinc alloy when the frequency is 10 Hz.
Figure 9A:
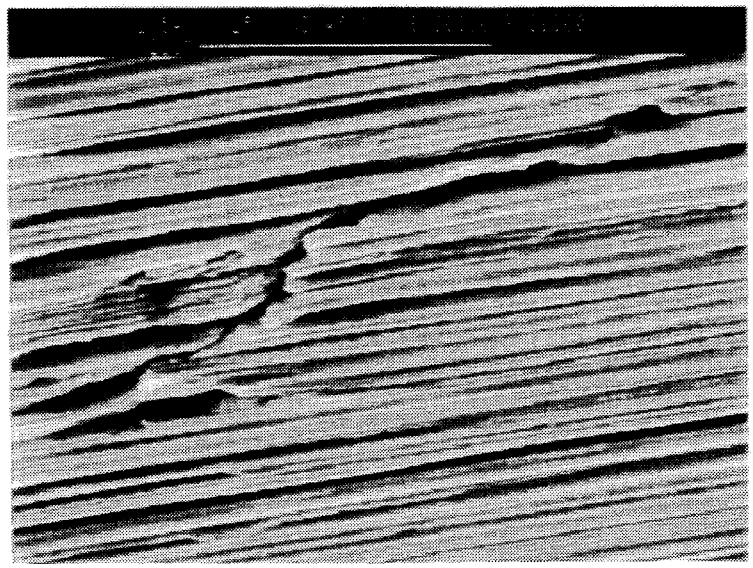
FIG. 9A is a photograph showing the outline of the copper-zinc alloy sample in stage (A) of FIG. 8 magnified 2540 times.
Figure 9B:
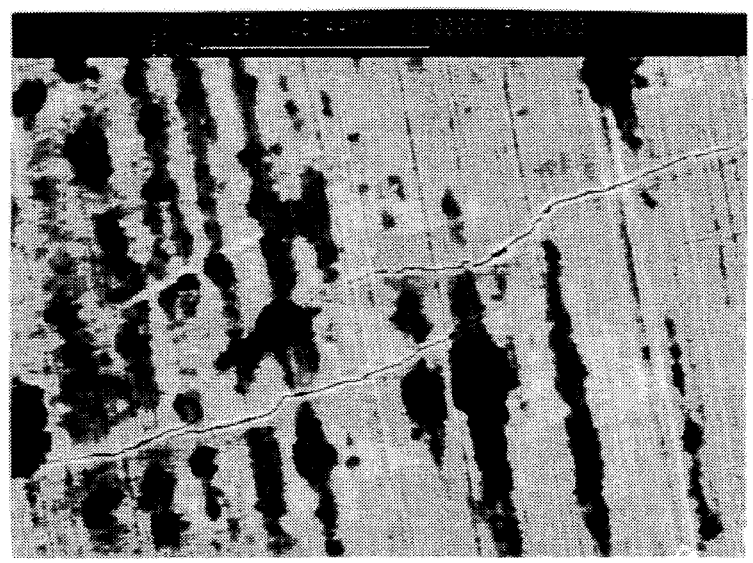
FIG. 9B is a photograph showing the outline of the copper-zinc alloy sample in stage (B) of FIG. 8 magnified 803 times.
Figure 9C:
FIG. 9C is a photograph showing the outline of the copper-zinc alloy sample in stage (C) of FIG. 8 magnified 296 times.

The testing frequency is fixed at 10 Hz. When the immersion time is greater than 100 seconds, the phase angle of the copper-zinc alloy sample begins to climb, and the phase angle increases as the crack propagates, the phase angle tends to be a stable value while the crack propagates through the sample, as shown in FIG. 8. FIG. 9A is a photograph showing the outline of the copper-zinc alloy sample in stage (A) of FIG. 8 magnified 2540 times, FIG. 9B is a photograph showing the outline of the copper-zinc alloy sample in stage (B) of FIG. 8 magnified 803 times, and FIG. 9C is a photograph showing the outline of the copper-zinc alloy sample in stage (C) of FIG. 8 magnified 296 times. The results indicate the phase angle can monitor the occurrence of the crack on the sample, and the phase angle increases as the crack propagates, as shown from the phase angle change in the three stages of FIG. 8, i.e. stage (A), stage.(B) and stage (C).

(3) The influence of the corrosive process

Figure 10:
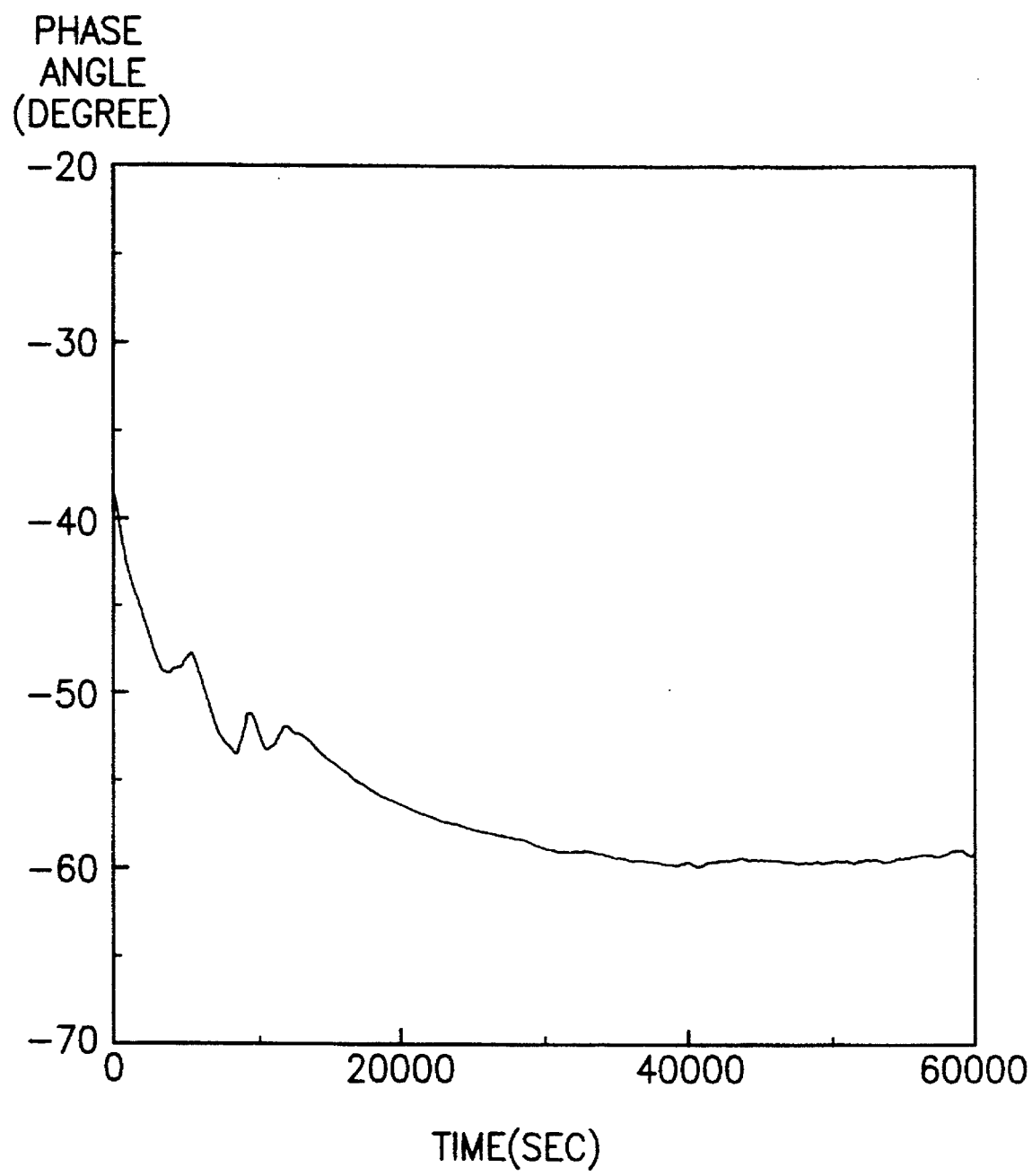
FIG. 10 is a relation diagram between phase angle and time for immersing the copper-zinc alloy sample into $Na_2SO_4$ solution when the frequency is 10 Hz.
Figure 11:
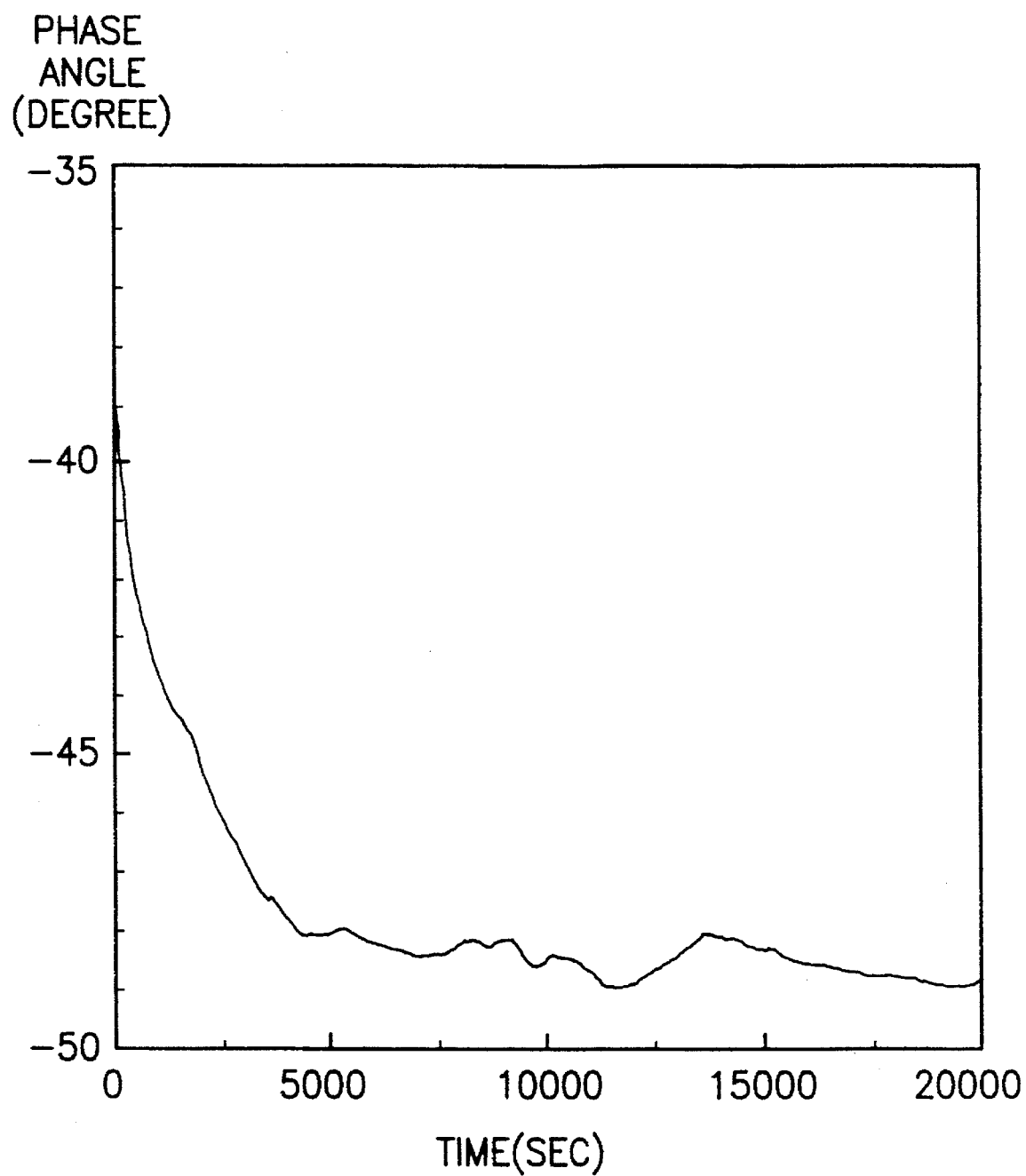
FIG. 11 is a relation diagram between phase angle and time for immersing the copper-zinc alloy sample into the buffered phosphate solution when the frequency is 10 Hz.

Immerse the copper-zinc alloy sample into $Na_2SO_4$ and a buffered phosphate solution respectively, measure the phase angle change of the sample while the frequency is set at 10 Hz, and the results indicate that the phase angle declines with time, as shown in FIG. 10 and FIG. 11 respectively. In other words, there is no crack propagation when the copper-zinc alloy sample is immersed in the $Na_2SO_4$ and the buffered phosphate solution respectively, thus the phase angle did not climb. After testing, the outline of the copper-zinc alloy sample is still the same.

(4) Appropriate frequency

Figure 12:
FIG. 12 is a magnified diagram of after immersing the copper-zinc alloy sample into $NH_4OH$ solution having copper powder.
Figure 13:
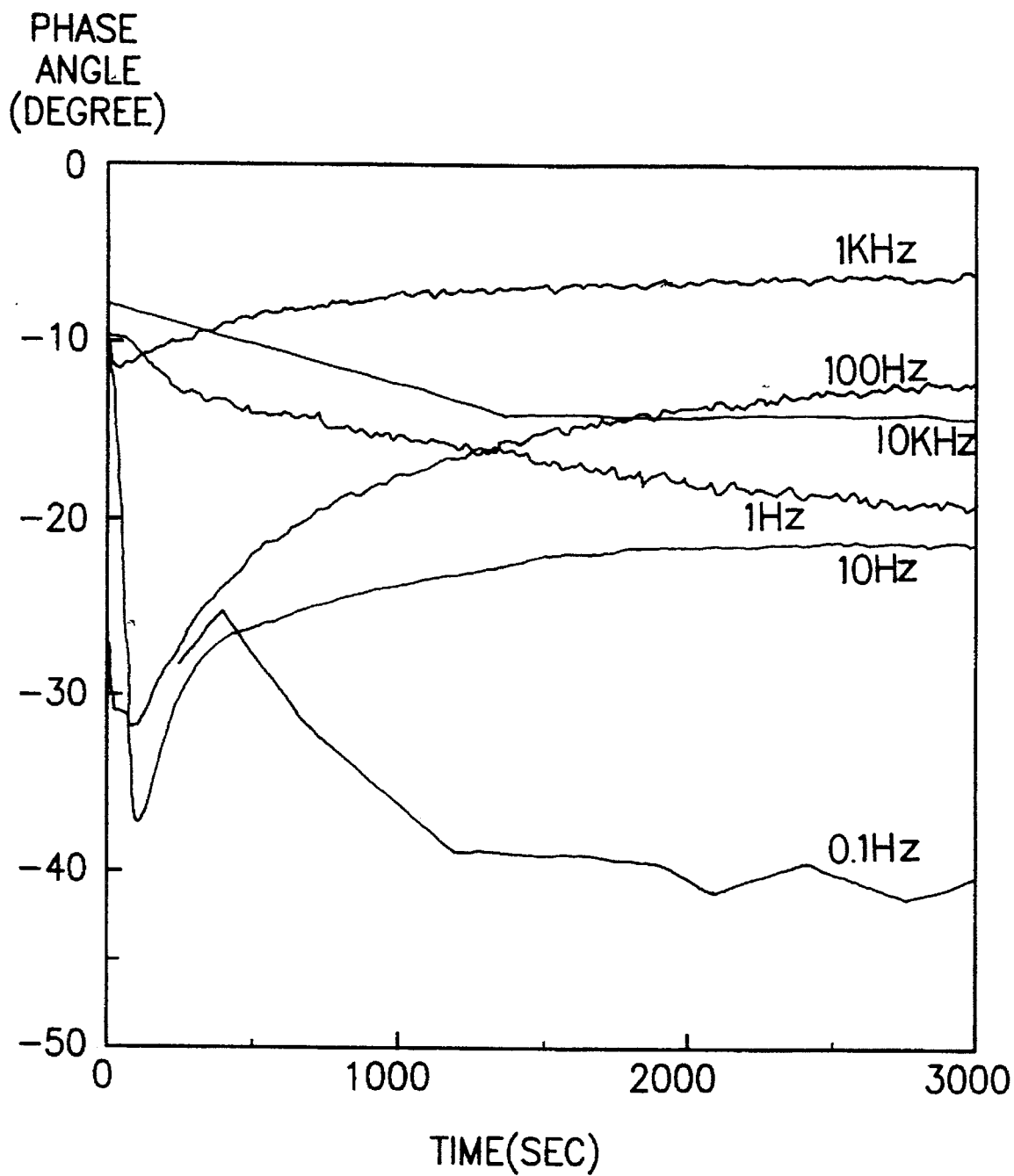
FIG. 13 is a relation diagram between phase angle and time for immersing the copper-zinc alloy sample into $NH_4OH$ solution having copper powder with different frequencies.

Immerse the U-type copper-zinc alloy sample into the $NH_4OH$ solution having copper powder, and measure the phase angle change with different frequencies (10 KHz to 0.1 Hz). After testing, the all tested samples cracked and one of the sample outlines is shown in FIG. 12. When the frequency, f, lies between 10 Hz and 100 Hz, i.e. 10 Hz$\leq$f$\leq$100 Hz, the phase angle can monitor the crack propagation successfully, as shown in FIG. 13.

It can be concluded from the above description that the method for monitoring cracks can be applied to the materials of different kinds and shapes independent of environmental factors when the sample is immersed in a solution having corrosive ions with an alternating current of the appropriate frequency range on the sample.

In addition, if the material to be tested is a reservoir or a flowing pipe (having solution inside), the present invention still can be applied to it as long as the auxiliary electrode can be disposed properly.

While the invention has been described in terms of what are presently considered to be the most practical and preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A method for monitoring cracks in a sample of materials, comprising the following steps of:

(a) preparing a solution capable of forming cracks in said sample;

(b) preparing said sample and an auxiliary electrode;

(c) making said sample and said auxiliary electrode contact said solution;

(d) preparing a frequency generator connecting said sample and said auxiliary electrode respectively;

(e) transmitting an alternating current signal from said frequency generator directly through said sample and said solution at a specified frequency;

(f) maintaining the frequency on said frequency generator at a constant frequency;

(g) measuring the phase angle of the alternating current signal being directly transmitted through said sample;

(h) analyzing the alternating current signal to detect changes in the phase angle resulting from a change in capacitance of said sample; and (i) computer correlating the changes in the phase angle of the alternating current signal to the changes in capacitance in said sample cause by formation of cracks in said sample.

2. A method for monitoring cracks in a sample of materials as set forth in claim 1 wherein said auxiliary electrode in step (b) is made of noble metal.

3. A method for monitoring cracks in a sample of materials as set forth in claim 2, wherein said auxiliary electrode is made of platinum.

4. A method for monitoring cracks in a sample of materials as set forth in claim 1, wherein said step (g) is performed by a signal analysis processing system.

5. A method for monitoring cracks in a sample of materials as set forth in claim 4, wherein said signal analysis processing system is a signal analyzer and a computer.

6. A method for monitoring cracks in a sample of materials as set forth in claim 1, wherein said solution capable of forming cracks in said sample in said step (a) is a solution containing chlorine ion or a solution containing sulfur environment.

7. A method for monitoring cracks in a sample of materials as set forth in claim 1, wherein said sample is made of stainless steel.

8. A method for monitoring cracks in a sample of materials as set forth in claim 1, wherein said frequency in said step (e) is chosen from a range of 20 to 200 Hz.

9. A method as set forth in claim 8, wherein said frequency is 20 Hz.

10. A method as set forth in claim 8, wherein said solution is $Na_2S_2O_3$.

11. A method for monitoring cracks in a sample of materials as set forth in claim 1, wherein said sample is made of copper-zinc alloy.

12. A method for monitoring cracks in a sample of materials as set forth in claim 1, wherein said frequency in said step (e) is chosen from a range of 10 to 100 Hz.

13. A method as set forth in claim 12, wherein said frequency is 10 Hz.

14. A method as set forth in claim 12, wherein said solution is $NH_4OH$.

* * * * *